US00RE35639E

United States Patent [19]

Vander Heyden et al.

[11] E Patent Number: Re. 35,639

[45] Reissued Date of Patent: Oct. 21, 1997

[54] METHOD AND APPARATUS FOR MEASURING RATIO OF MASS FLOW RATES AND ENERGY FLOW IN A GAS PIPELINE

[75] Inventors: William H. Vander Heyden, Mequon, Wis.; William H. Clingman, Jr., deceased, late of Dallas, Tex., by Mary Jane Wheeler Clingman, legal representative

[73] Assignee: Badger Meter, Inc., Milwaukee, Wis.

[21] Appl. No.: 420,254

[22] Filed: Apr. 11, 1995

Related U.S. Patent Documents

Reissue of:

[64] Patent No.: 5,201,581
Issued: Apr. 13, 1993
Appl. No.: 793,753
Filed: Nov. 18, 1991

[51] Int. Cl.[6] ..... G01N 25/22; G01F 1/00; G01F 9/00

[52] U.S. Cl. ..... 374/36; 374/37; 73/196; 73/863.03; 73/863.61

[58] Field of Search ..... 374/36, 37; 73/861, 73/196, 863.03, 863.61

[56] References Cited

U.S. PATENT DOCUMENTS

| | | | |
|---|---|---|---|
| 3,777,562 | 12/1973 | Clingman | 374/37 |
| 4,062,236 | 12/1977 | Clingman | 374/37 |
| 4,125,018 | 11/1978 | Clingman | 374/37 |
| 4,125,123 | 11/1978 | Clingman | 374/37 |
| 4,285,245 | 8/1981 | Kennedy | 73/861 |
| 4,351,614 | 9/1982 | Garnier | 374/37 |
| 4,380,400 | 4/1983 | Searle | 374/37 |
| 4,396,299 | 8/1983 | Clingman et al. | 374/37 |
| 4,446,748 | 5/1984 | Clingman et al. | 73/863.03 |
| 4,527,435 | 7/1985 | Hall et al. | 73/863.03 |
| 4,562,744 | 1/1986 | Hall et al. | 73/861.02 |
| 4,614,721 | 9/1986 | Goldberg | 374/37 |
| 4,677,841 | 7/1987 | Kenedy | 73/30 |
| 4,845,976 | 7/1989 | Johnson et al. | 374/36 |
| 5,016,482 | 5/1991 | Clingman et al. | 73/863.61 |

FOREIGN PATENT DOCUMENTS

| | | | |
|---|---|---|---|
| 0864113 | 2/1971 | Canada | 73/196 |
| 0326494 | 8/1989 | European Pat. Off. | 374/37 |
| 2664975 | 1/1992 | France . | |
| 1110893 | 7/1961 | Germany | 73/196 |
| 2099589 | 12/1982 | United Kingdom | 374/36 |

*Primary Examiner*—Diego F. F. Gutierrez
*Attorney, Agent, or Firm*—Quarles & Brady

[57] ABSTRACT

The present invention is a method and apparatus for monitoring in real time the mass and energy flow rate of a gas through a pipeline. The invention determines the mass flow ratio of a pipeline gas flowing through a pipeline compared to sample gas tapped from the pipeline line when the volumetric flow of pipeline gas through the pipeline is measured by a linear flow meter. Sample gas tapped from the pipeline is flowed to a chamber having a section with a fixed volume until the pressure in the chamber section is substantially equal to the pipeline gas pressure. The sample gas is maintained at substantially the same temperature as the gas in the pipeline while the sample gas is in the chamber section. A timer measures the time interval for the sample gas to flow from the chamber section at a selected rate for a calculated pressure drop the selected rate being controlled by a flow controller. The mass flow ratio is computed using the measured time interval and a signal from the linear flow meter. The energy flow rate of the pipeline gas is determined by measuring the energy flow rate of the sample gas and relating that value to the mass flow ratio of the pipeline gas compared to the sample gas.

47 Claims, 3 Drawing Sheets

SAMPLE GAS PRESSURE IN FIRST CHAMBER

METHOD AND APPARATUS FOR MEASURING RATIO OF MASS FLOW RATES AND ENERGY FLOW IN A GAS PIPELINE

Matter enclosed in heavy brackets [ ] appears in the original patent but forms no part of this reissue specification; matter printed in italics indicates the additions made by reissue.

*BACKGROUND OF THE INVENTION*

*1. Field of the Invention*

The present invention relates to instrumentation for measuring in real time the mass *flow rates* and the energy [flow rate] *flows* of gas through a [pipe] *pipeline*. [In particular, it] *The invention also* relates to apparatus for measuring the ratio of the mass flow rate of pipeline gas flowing through a pipeline compared to *the* sample gas flowing through the apparatus. The invention also relates to apparatus for measuring [the] energy [flow] *flows and energy flow* rate [of gas through a pipeline].

*2. Description of the Background Art*

Mass and energy flow rates of gas through pipelines are normally calculated in flow computers from contemporaneous measurements of several gas parameters. Generally, for measuring mass flow rate, the volumetric flow rate of the gas is measured and gas temperature, pressure, and composition are measured to enable the gas density and, thus, the mass flow rate to be calculated from the volumetric flow rate. The composition of the gas is normally measured by gas chromatography. When the operating conditions are such that the super-compressibility of the gas in the calculation of density cannot be ignored, supercompressibility properties are normally estimated from either the virial equations of state for the gas or from precalculated correlations such as NX-19.

Knowledge of the values of the virial coefficients of particular gas compositions is quite limited in the art, so the calculation of gas density from the virial equations of state is not always possible. Furthermore, correlations such as NX-19, for natural gas, are approximate and the accuracy of extrapolations from such correlations is questionable. It is therefore difficult to obtain accurate real time density values for calculating the mass flow rates of gas flowing through a pipeline with present day equipment.

When energy flow rate, in addition to mass flow rate, is desired, the energy content of the gas must also be determined. The energy content of the gas (energy per unit mass or volume) can be determined either indirectly by measuring the composition of the gas or by direct measurements such as the stoichiometric ratio method. Once the energy content of the gas is determined, the energy flow rate of the gas through the pipeline can be calculated by multiplying the energy content of the gas (e.g. BTU/lb) by the mass flow rate of the gas (e.g. lbs./hr.).

Each of these measurements discussed above (volumetric flow, temperature, pressure, and composition) are measured separately and introduce an opportunity for measurement error. The aggregation of these measurement errors can be quite substantial and distort mass or energy flow calculations. To minimize measurement errors, each piece of instrumentation must be maintained and calibrated periodically. Moreover, additional errors can be introduced within the flow computer from calculations or inaccurate formulas or correlations.

In U.S. Pat. No. 4,396,299, Clingman disclosed a method and apparatus for measuring [the rate of] *energy flow rate and total energy flow* of *a* gas through a pipeline that did not require gas density to be measured either directly or indirectly. [That invention, which flows sample gas through a calibrated capillary tube, is able to measure the energy flow of pipeline gas through a pipeline by sampling a constant fraction of the pipeline gas and] *In Clingman, the pipeline gas was sampled as a sample flow rate that was constantly proportional to the volume flow rate in the pipeline. To maintain this condition, Clingman used a differential pressure sensor in a line connected between the gas pipeline and the sample line to maintain zero pressure differential between the gas pipeline and the sample gas line. The energy flow rate was determined by* measuring the mass flow of air which [is] *was* burned with the sample gas at maximum flame temperature. [The mass flow rate of the sample gas varies in direct proportion with the mass flow rate of the gas through the pipeline.] *Clingman, U.S. Pat. No. 4,396,299, col. 9, lines 21–31, teaches that flow rates through the main pipeline can be integrated to determine total flows, and conversely, that a time derivative of these flows is a flow rate.*

*One object of the present invention is to provide a flow meter for measuring volume and energy flows, which is not limited by the requirement to sample gas at a rate that is constantly proportional to the flow rate in the pipeline.*

[In a copending patent application entitled "Method and Apparatus for Measuring Mass Flow and Energy Content Using a Differential Pressure Meter" filed on Nov. 4, 1991, Ser. No. 07/787,188, William Vander Heyden explains a method and apparatus wherein the mass flow rate of the sample gas does not vary with the mass flow rate of the gas through the pipeline.

The invention disclosed in U.S. Pat. No. 4,396,299 and the invention disclosed by Vander Heyden in copending patent application entitled "Method and Apparatus For Measuring Mass Flow and Energy Content Using A Differential Pressure Meter" can only be used in connection with an in-line differential pressure volumetric meter. That is, a device installed in the pipeline that causes a pressure differential to occur in the pipeline gas as the pipeline gas flows across the device. Such in-line devices produce signals proportional to the velocity squared. As such, these inventions do not operate in conjunction with flow meters that produce signals which are linearly proportional to flow velocity. These are many types of linear flow meters including but not limited to turbine, vortex, rotary, diaphragm or ultrasonic meters.]

SUMMARY OF THE INVENTION

The present invention [is] *provides* a method and apparatus for determining the ratio of the mass flow rate of *a* pipeline gas [flowing through a pipeline compared] to the mass flow rate of a sample gas[tapped from the pipeline]. The invention allows this determination to be made in real time.

[Sample gas is tapped from the pipeline and flows to a chamber having a section with a fixed volume. While the sample gas is in the fixed-volume chamber section, the sample gas must be maintained at substantially the same temperature as the gas in the pipeline.

A valve controls the flow of sample gas to the chamber section. When the valve is opened, sample gas flows into the chamber section until the gas pressure in the chamber section becomes equal to the gas pressure in the pipeline. The valve is then closed and stops the flow of sample gas into the chamber section. Sample gas flows from the chamber section after the valve is closed (but sample gas may also flow from the chamber section at a slow rate before the valve is closed). When the sample gas pressure in the chamber section drops below a starting pressure, a timer begins. The timer measures a time interval $t_m$ for the sample gas pressure in the chamber section to fall from the starting pressure to a stopping pressure. The average of the starting pressure and the stopping pressure is mathematically related to the pipeline gas pressure. During the time interval $t_m$, the sample gas flows from the chamber section at a selected rate as controlled by a flow controller that is located downstream of the chamber.]*According to a first aspect of the invention, a sample of the gas is flowed at pipeline temperature and pressure to a chamber of a known volume. The gas is then released under flow control and the derivative of pressure with respect to time is monitored to generate a resulting time interval signal, $t_m$. This is used to calculate the ratio of the mass flow rate of the pipeline gas to the mass flow rate of the sample gas.*

Based on the time interval, $t_m$, proportionality constants, and [information] a signal from a flow meter that [transmits a signal which] is linear to the velocity of the flow of the pipeline gas through the pipeline (e.g. a turbine or a vortex meter), the ratio of the mass flow rate of pipeline gas through the pipeline compared to the mass flow rate of the sample gas can be determined in a control system (e.g., *a* computer).

The *first aspect of the* present invention requires only two measurements for determining the mass flow ratio: the time interval $t_m$ and a signal from a linear flow meter. The present invention alleviates the need to consider the effects of supercompressibility, temperature, pressure, density or composition because the critical measurement (i.e. the time interval $t_m$) is made when the sample gas is at a condition related to pipeline conditions.

An object of the present invention is to measure the mass flow ratio without fluctuating the sample gas flow rate exiting the system. The present invention accomplishes this object by using a flow controller to maintain the sample gas exit flow rate at a rate set by the control system. [The present invention also contemplates using the apparatus described above with apparatus for measuring the energy content of the sample gas to determine the energy flow rate of combustible gas through a pipeline.]

*According to a second aspect of the invention, the invention also provides a method and apparatus for determining energy flow rate and total energy flow by sampling volumes of the pipeline gas at pipeline conditions and combusting the samples of the gas to determine energy flow in the pipeline.*

[When the present invention is used to measure the energy flow rate, it is preferred that the sample gas be fed to a burner after the sample gas exits the flow controller, and be burned with an amount of air at a maximum flame temperature. When the sample gas is burned at the maximum flame temperature, the energy flow rate of the sample gas is proportional to the amount of air burning the sample gas.

The energy flow rate of the pipeline gas through the pipeline is determined from calculations involving the air mass flow rate, the time interval ($t_m$), and signals from the linear flow meter monitoring the flow of pipeline gas.

The present invention allows the energy flow rate of pipeline gas to be determined with precision from three measurements: the air mass flow rate to the burner, the time interval for the above identified chamber section pressure decay, $t_m$, and the pipeline gas flow data from the linear flow meter.]

The present invention [therefore] allows accurate real time determination of the energy flow rate of a pipeline gas flowing through a pipeline without the need to compensate for the effects of gas temperature, pressure, density, composition or supercompressibility. It also allows for the energy flow rate of pipeline gas to be monitored accurately without substantially interfering with the pipeline gas flow.

The present invention further provides measurement stability for the flame temperature and thus assures that the flame temperature can be maximized. This is important because flame temperature must be maximized so that, for saturated hydrocarbon gases, the flow of air burning the sample gas is proportional to the energy content of the sample gas. The flame is promoted to burn at the constant height because the sample gas flows from the flow controller to the burner at a selected flow rate. A thermocouple measuring the flame temperature can therefore be located in a consistent position within the flame and measure relative flame temperature more accurately.

Another object of the present invention is to measure the energy flow rate through each of the multiple pipeline runs at a pipeline metering station with a single energy measuring apparatus. The present invention can accomplish this object by systematically sampling each run sequentially in time. It is required, however, that a separate linear flow meter to installed in each run to operate in this mode.

The invention also includes a method for measuring the mass flow ratio of the pipeline gas through the pipeline compared to the sample gas tapped from the pipeline and a method for measuring the energy flow rate of the pipeline gas through the pipeline. Both methods involve measuring the volumetric flow rate of the pipeline gas through the pipeline with a linear flow meter. They also involve flowing a sample of gas to a chamber having a section with fixed volume and maintaining the temperature of the sample gas at substantially the same temperature as the pipeline gas in the pipeline when the sample gas is in the chamber section. The flow of sample gas to the chamber section is stopped when the pressure in the chamber section reaches the pressure of the pipeline gas. After the flow of sample gas to the chamber section is stopped, the sample gas is flowed from the chamber section thereby reducing the sample gas pressure in the chamber section. A starting pressure is determined as a function of the pipeline gas pressure. An interval of time for the sample gas to flow from the chamber section at a selected rate, beginning when the sample gas pressure in the chamber section drops below the starting pressure and ending when the sample gas in the chamber section drops below a stopping pressure, is timed. Based on the interval of time and a signal from the linear flow meter, the mass flow ratio can be calculated in a control system. The method for measuring the energy flow rate of a pipeline gas through a pipeline is generally the same as described above but also includes measuring the energy content of the sample gas.

The foregoing advantages of the present invention will appear from the following description. In the description, references are made to the accompanying drawings which form a part hereof and in which a preferred embodiment of the present invention is shown by way of illustration. Such embodiment does not necessarily represent the full scope of the invention however.

DESCRIPTION OF THE PREFERRED EMBODIMENT

One class of meters for measuring the volumetric flow of gas through a pipeline is linear flow meters, that is meters, such as turbine or vortex meters, which produce a signal directly proportional to flow velocity. Linear flow meters are different than another class of volumetric flow meters referred to as differential pressure flow meters because differential pressure meters produce a signal proportional to pressure differentials which are proportional to the velocity squared and not linear to flow velocity. The present invention is used in conjunction with one or more linear flow meters.

Figure 1:
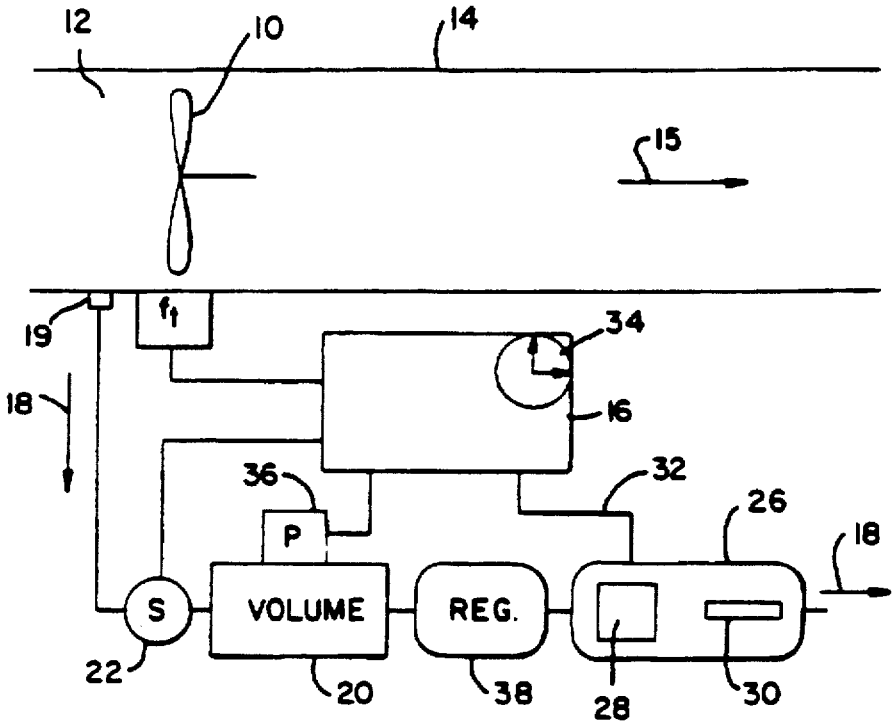
FIG. 1 is a schematic drawing showing the fundamental apparatus of the present invention.

In FIG. 1, the present invention is used in conjunction with a turbine meter 10. The turbine meter 10 measures the volumetric flow rate of a pipeline gas 12 flowing through a pipeline 14 in the direction of arrow 15. The turbine meter 10 communicates the volumetric flow rate of the pipeline gas 12 as the ratio of turbine frequency $f_t$ compared to a turbine meter factor $K_t$. The turbine meter factor $K_t$ is normally stored in a control system 16; whereas, the turbine frequency $f_t$ is relayed to the control system 16 periodically.

In the preferred embodiment, the control system 16 is an electrical system utilizing conventional switching techniques to operate the instrumentation in accordance with the procedures of the invention. If desired, the control system 16 may employ conventional solid state microprocessor techniques, such as: an electronic timing device or clock, an analog-to-digital converter, output signal amplifiers, storage memory for the control program, an arithmetic unit for dividing, and the like.

A sample of gas 18 is tapped upstream of the flow meter 10 at point 19. The sample gas 18 flows into a first fixed-volume chamber 20. The volume of the chamber is small, about 20 cubic centimeters. The sample gas 18 must be maintained at substantially the same temperature as the pipeline gas 12 when it is in the first chamber 20. If the temperature of the sample gas 18 is maintained at substantially the same temperature as the pipeline gas 12, the need to compensate for the effects of supercompressibility can be avoided as will be discussed below.

Figure 2:
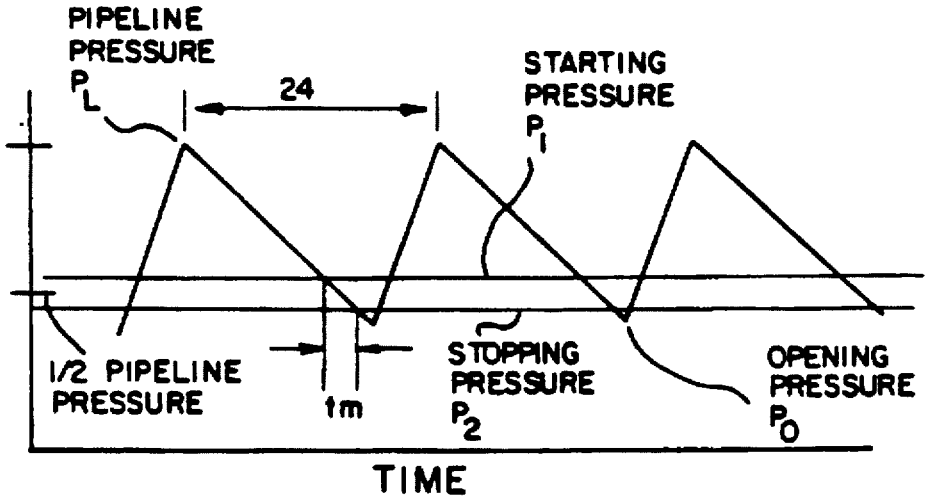
FIG. 2 is a plot of a sample gas pressure within a chamber section with a fixed-volume as a function of time when the present invention as shown in FIG. 1 is operating.

The flow of sample gas 18 into the first chamber 20 is controlled by a first solenoid valve 22. Referring to FIG. 2, the first solenoid valve 22 is open at the beginning of a sampling cycle 24 and sample gas 18 flows into the first chamber 20. When the pressure in the first chamber 20 reaches a pressure $P_L$ of the pipeline gas 12 in the pipeline 14, the first solenoid valve 22 closes and terminates the flow of sample gas 18 into the first chamber 20. The sample gas 18 may be held within the first chamber 20 at the pipeline pressure $P_L$ to assure that the sample gas 18 is substantially the same temperature and density as the pipeline gas 12.

Referring again to FIG. 1, a flow controller 26 for maintaining a selected flow of sample gas 18 from the first chamber 20 is located downstream of the first chamber 20. Flow controllers are known in the art and an electronically adjustable pressure regulator, or I/P converter 28, followed by a capillary tube 30 is suitable for this application. The I/P converter 28 precisely determines the sample gas 18 pressure in response to an electrical signal 32 from the control system 16 (typically ranging from 4 to 20 ma direct current), and thus determines the flow rate of sample gas 18 through the capillary tube 30.

Referring again to FIG. 2, the flow controller 26 allows sample gas 18 to flow from the first chamber 20 at a selected rate. As the sample gas 18 flows from the first chamber 20 after the first solenoid valve 22 closes, the pressure within the first chamber 20 drops. When the chamber pressure reaches a starting pressure $P_1$, a timer 34 (see FIG. 1) starts. When the pressure in the first chamber 20 drops to a stopping pressure $P_2$, the timer 34 is stopped and the time interval $t_m$ is recorded. The chamber 20 pressure continues to drop until it reaches an open pressure $P_o$ at which time the first solenoid valve 22 opens and a new sampling cycle 24 begins. This type of apparatus is similar to the invention disclosed in U.S. Pat. No. 4,285,245 issued to Kennedy on Aug. 25, 1981.

Referring again to FIG. 1, a pressure sensor 36 senses the pressure within the first chamber 20. Preferably, the pressure sensor 36 is a strain gauge type sensor with an electrical output, i.e. a pressure transducer, but other types of pressure sensors or transducers may be used if desired.

The pressure sensor 36 communicates with the first solenoid valve 22 and with the timer 34, preferably through the control system 16. When the pressure sensor 36 senses that the pressure in the first chamber has reached the pipeline pressure $P_L$, it communicates to close the first solenoid valve 22. When the sensor 36 senses that the pressure in the first chamber 20 has dropped below the starting pressure $P_1$, it communicates to the timer 34 to begin timing. Likewise, the sensor communicates with the timer 34 to stop timing when the pressure in the first chamber 20 drops below the stopping pressure $P_2$. The sensor 36 also communicates with the first solenoid valve 22 to open the valve 22 when the pressure in the first chamber 20 reaches the opening pressure $P_o$.

Although it is not necessary in all applications, a pressure regulator 38 may be installed in line between the first chamber 20 and the flow controller 26. A pressure regulator 38 may be necessary, for example, when the pipeline gas 12 pressure $P_L$ is high.

In order for the accuracy of the present invention to be substantially independent of the supercompressibility of the pipeline gas 12 two conditions must exist within the first chamber 20:

1) The temperature and pressure of the sample gas 18 within the first chamber 20, at the time the first solenoid valve 22 is closed, must be substantially equal to the temperature and pressure of the pipeline gas 12 in the pipeline 14; and 2) The starting pressure $P_1$ must be about one-half of the pressure $P_L$ of the pipeline gas 12 in the pipeline 14.

Figure 3:
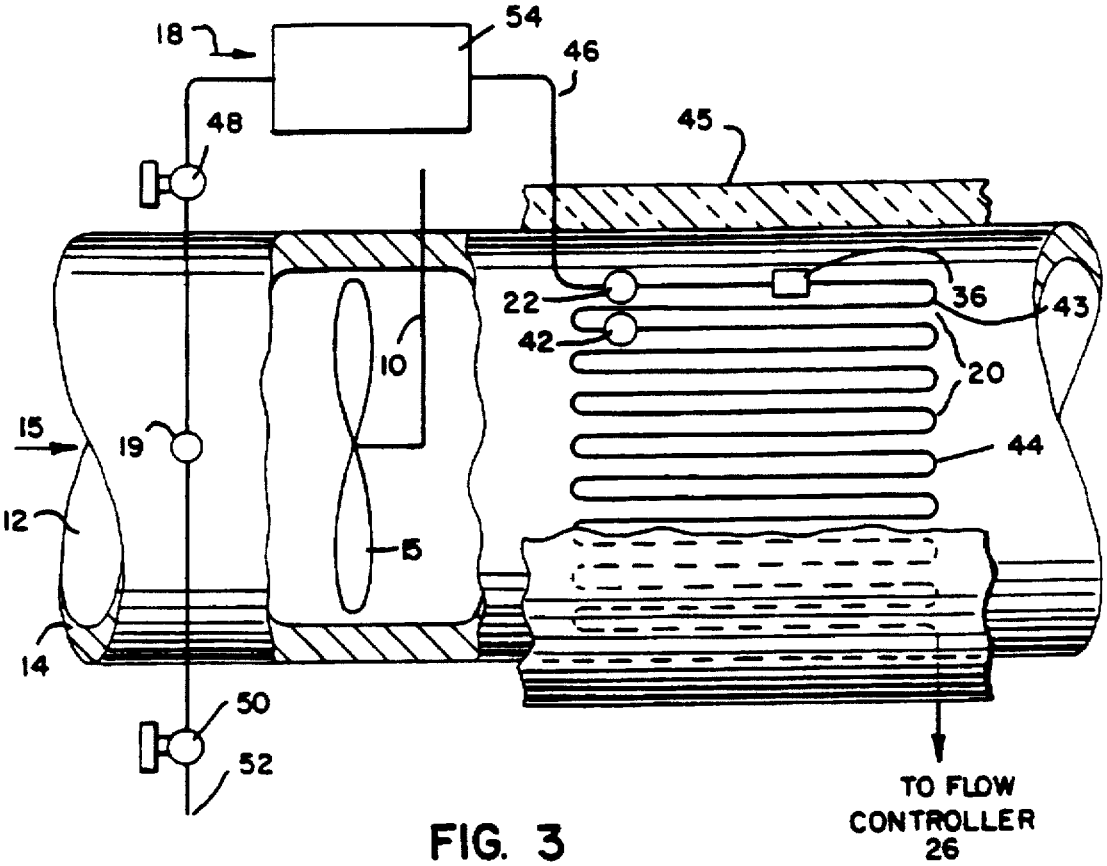
FIG. 3 is a schematic drawing showing an embodiment of the present invention in which i) the sample gas pressure in the fixed-volume chamber section can be reduced to a starting pressure more rapidly, and ii) the temperature of the sample gas in the fixed-volume chamber section is maintained substantially equal to the temperature of the pipeline gas flowing through the pipeline.

The embodiment of the present invention that is depicted in FIG. 3 uses a serpentined hollow coil 20' as the first fixed-volume chamber 20 to facilitate the occurrence of the two conditions stated above. Referring to FIG. 3, the serpentined hollow coil 20' is located immediately downstream of the first solenoid valve 22. A second solenoid valve 42 is located downstream in the serpentined hollow coil 20'. The volume within the hollow coil 20' that is enclosed by the solenoid valves 22 and 42 is a first [section 43 of the first] chamber [20] *43*. The volume within the hollow coil 20' after the second solenoid 42 and before the flow controller 26 is a second [section] *chamber* 44 of the [first chamber] *hollow coil* 20'. The sample gas 18 flows from the second [section] *chamber* 44 continuously at a rate selected by the flow controller 26.

The hollow coil 20' is mounted in intimate contact with the pipeline 14 and serpentines back and forth across the outer surface of a portion of the pipeline 14. Insulation 45 should be placed around the hollow coil 20', the solenoid valve 22 and 42, and the pipeline 14. A heat transfer compound may also be used to facilitate temperature equalization. With this configuration, the temperature of the sample gas 18 within the first [section] *chamber* 43 [of the first chamber 20] is maintained at substantially the same temperature as the temperature of the pipeline gas 12 flowing through the pipeline 14.

The second solenoid valve 42 is closed when sample gas 18 is filling the first [section] *chamber* 43 of the hollow coil 20' to pipeline pressure $P_L$. When the sample gas 18 pressure in the first [section] *chamber* 43 reaches $P_L$, the first solenoid valve 22 closes and the second solenoid valve 42 opens. The sample gas 18 pressure in the first [section] *chamber* 43' reduces quickly because the sample gas 18 pressure in the second [volume] *chamber* 44 is less than the sample gas 18 pressure in the first section 43 at that instant. The volume of the second [second] *chamber* 44 is such that the pressure in both chambers will stabilize at a pressure slightly higher than the starting pressure $P_1$. The pressure in both [sections] *chambers* 43 and 44 combined then decays to $P_1$ at which time the timer 34 begins and measures the time interval $t_m$ for the pressure in both [sections] *chambers* 43 and 44 to decay from the starting pressure $P_1$ to the stopping pressure $P_2$.

In this embodiment, [where the] *with* first chamber [has a first] 43 and a second *chamber* 44 [section], it is necessary for the sample gas pressure in the first [section] chamber 43 to reach $P_L$ while being maintained at substantially the same temperature as the pipeline gas 12, but it is not necessary for the sample gas pressure in the second [second] chamber 44 to reach $P_L$. This configuration allows rapid containment of the sample gas 18 within the fixed volume of the first [section] chamber 43 of the hollow coil 20' at pipeline pressure $P_L$ and alleviates the need to wait for the sample gas 18 pressure to slowly decay to the starting pressure $P_1$. Moreover, the second [section] chamber 44 of the hollow coil 20' has a much larger volume than the first [section] chamber 43 (i.e. about 12 fold) and thus the sample gas 18 pressure within the second [section] chamber 44 does not fluctuate substantially. The flow rate through the flow controller 26 is thus easier to maintain at the selected rate.

Still referring to FIG. 3, an arching sample gas feed 46 along with a valve 48 and a valve 50 are used to remove debris from the sample gas 18 before the sample gas 18 flows to the hollow coil 40. The low velocity in the rising section containing the valve 48 precludes particles from reaching the arch in the arching sample gas feed 46. Instead, the particles fall into a lower section of the pipe containing the valve 50. Periodically, the valve 50 can be opened to blow the collected debris from the lower section of the pipe through a blow hole 52. A filter 54 is also installed on the arching sample gas feed 46 to remove debris from the sample gas 18.

The following analysis is recited to emphasize the significance that $$P_1 = \frac{P_L}{2}$$

and to also explain additional features of the preferred embodiment of the invention that further improve the accuracy of the invention.

The total derivative of pressure with respect to time must account for density changes as well as molar flow and is given by:

$$\left(\frac{dP}{dt}\right)_T = \frac{RT\left(Z + \left(\frac{\delta Z}{\delta \rho}\right)_T\right)}{M_w V}\,\omega_m \tag{1}$$

where $$\left(\frac{dP}{dt}\right)_T$$

is the total derivative of pressure with respect to time at constant temperature T, R is the real gas constant, V is the volume of the first fixed-volume chamber 20 (or the volume of the first section 43 of the hollow coil 20' if the embodiment in FIG. 3 is used), $M_W$ is the molecular weight of the sample gas 18, $\omega_m$ is the mass flow rate of the sample gas 18, Z is the supercompressibility constant for the gas, and $$\left(\frac{\delta Z}{\delta \rho}\right)_T$$

is the partial derivative of Z at constant temperature T with respect to the density of the gas ρ.

The supercompressibility constant Z, which describes the dynamics of supercompressible gas, can be closely approximated by expanding the virial equation of state through the first three terms:

$$Z = 1 + bP + cP^2 = 1 + B\rho + C\rho^2 \tag{2}$$

where ρ is gas density, P is the absolute gas pressure, B and C are the second and third density viral coefficients of the gas, and b and c are the second and third pressure virial coefficients of the gas. The virial coefficients depend on gas temperature and composition. The density virial coefficients are related to the pressure virial coefficients according to generally accepted mixing rules:

$$b = \frac{B}{RT} \tag{3a}$$

$$c = \frac{(C - B^2)}{R^2 - T^2} \tag{3b}$$

where R is the real gas constant and T is the absolute temperature of the gas.

It follows from Eqs. (1), (2) and (3) that the total derivative $$\left(\frac{dP}{dt}\right)_T$$

for the sample gas is:

$$\left(\frac{dP}{dt}\right)_T = \frac{RT(1+2bP_1+(3c+b^2)P_1)}{M_wV}\,\omega_m \tag{4}$$

In the present invention, the derivative $$\left(\frac{dP}{dt}\right)_T$$

is represented by:

$$\left(\frac{dP}{dt}\right)_T = \frac{P_1-P_2}{t_m} \tag{5}$$

where $t_m$ is the time interval for the sample gas pressure in the first chamber to drop from $P_1$ to $P_2$. There is no requirement that P2 be a specific pressure other than P2 be less than P1 and selected to appropriately measure $$\left.\frac{dP}{dt}\right|_{P=P_1/2}$$

As shown in FIG. 2, P1 is greater than about one-half of the pipeline gas pressure in the pipeline while P2 is less than about one-half of the pipeline gas pressure in the pipeline. Substituting Eq. (5) into Eq. (4) and solving for the mass flow rate of the sample gas 18, $\omega_m$, results in:

$$\omega_m = \frac{M_wV(P_1-P_2)}{RT(1+2bP_1+(3c+b^2)P_1^2t_m)} \tag{6}$$

Now, the mass flow rate of the pipeline gas 12 is given by:

$$\omega_t = \frac{\rho f_t}{K_t} \tag{7}$$

where $f_t$ is the frequency signal that the turbine meter 10 communicates to control system 16, and $K_t$ is the turbine meter calibration constant relating turbine frequency $f_t$ to volumetric flow rate (i.e. cycles/unit volume).

Using the real gas law and the virial equations of state, Eq. (7) becomes:

$$\omega_t = \frac{f_t}{K_t}\,\frac{P_LM_w}{RT(1+bP_L+cP_L^2)} \tag{8}$$

where $P_L$ is the absolute pressure of pipeline gas 12. Dividing Eq. (8) by Eq. (5) results in:

$$\frac{\omega_t}{\omega_m} = \frac{P_Lf_tt_m(1+2bP_1+(3c+b^2)P_1^2}{K_tV(P_1-P_2)(1+bP_L+cP_L^2)} \tag{9}$$

From Eq. (9), it is apparent that the effects of supercompressibility, first represented by the second pressure virial coefficient b, are minimized if $P_1$ is approximately equal to $P_L/2$. The accuracy of the invention is not compromised significantly provided that the starting pressure $P_1$ is within a few percent of half the pipeline pressure $P_L$ because the second virial coefficient b is of the order $10^{-3}$.

Figure 4:
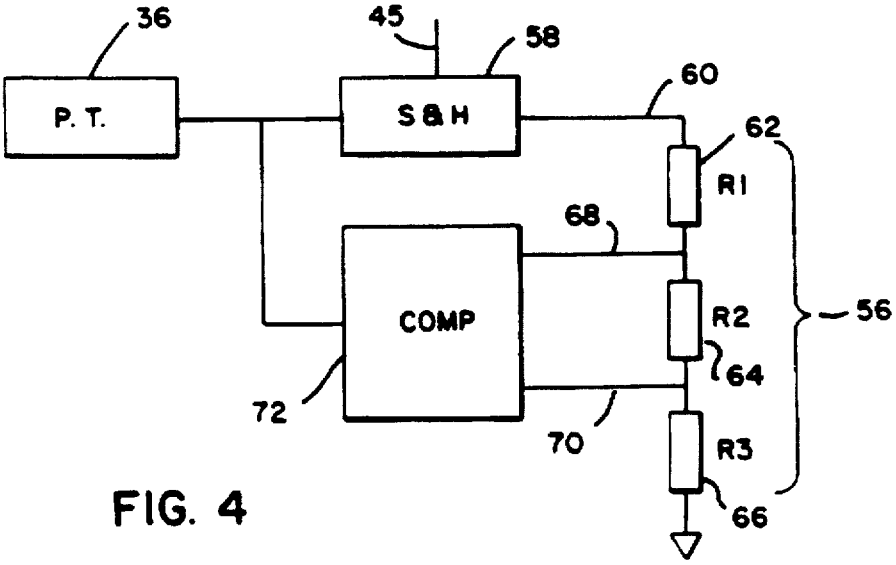
FIG. 4 is a schematic drawing showing the circuitry for controlling the starting and the stopping of a timer.

Referring to FIG. 4, the starting $P_1$ and the stopping $P_2$ pressures are determined by a resistor string 56. The pressure sensor 36 senses the pressure in the first chamber 20 (or in the first section 43 or the hollow coil 20' if the embodiment shown in FIG. 3 is used) and communicates the data to an associated sample and hold circuit 58 and to the control system 16. The control system 16 determines when the sample gas 18 pressure in the first chamber 20 stabilizes at a maximum pressure, i.e. at the pipeline gas 12 pressure $P_L$, and sends a signal 45 indicating that maximum pressure to the sample and hold circuit 58. The sample and hold circuit 58 memorizes the value of the maximum pressure in the first chamber 20' for each sampling cycle 24. The circuit 58 is cleared at the end of each sampling cycle 24 after it receives a signal that the first solenoid valve 22 has opened.

An output voltage 60 from the sample and hole circuit 58 represents the maximum chamber pressure (i.e. $P_L$) and leads to the grounded resistor string 56. The output voltage 60 is split by the resistors 62, 64, and 66. The output voltage 60 drops across resistor 62 to the $P_1$ reference voltage 68 and further drops across resistor 64 to the $P_2$ reference voltage 60. The resistance of the resistor 62, R1, is equivalent to the sum of the resistance of resistors 64 and 66, R2+R3, so that the starting pressure $P_1$ is $P_L/2$. A ratio $$Kp = \frac{P_L}{(P_1-P_2)}$$

is then represented by $$\frac{R1+R2+R3}{R2}.$$

The $P_1$ and $P_2$ reference voltages (68 and 70) are stored in a comparator 72 which compares these values to a signal from the pressure sensor 36. When the pressure sensor 36 signals that the pressure in the first chamber 20 has dropped to $P_1$, the comparator 72 activates the timer 34. When the pressure drops to $P_2$, the comparator 72 signals the timer 34 to stop.

Equation (9) can then be written as:

$$\frac{\omega_t}{\omega_m} = \frac{K_{Pf_t}t_m\left(1+bP_L+\frac{(3c+b^2)}{4}P_L^2\right)}{K_tV(1+bP_L+cP_L^2)} \tag{10}$$

and since higher order terms are very small, Eq. (10) can be reduced to:

$$S = \frac{\omega_t}{\omega_m} = \frac{K_{Pf_t}t_m}{K_tV}\left(1+\frac{(b^2-c)}{4}P_L^2\right) \tag{11}$$

where S is a splitting ratio.

$$\frac{\omega_t}{\omega_m} = \frac{P_Lf_t}{K_tV}\left(\left.\frac{dP}{dt}\right|_{P=P_L/2}\right)^{-1}\left(1+\frac{(b^2-c)}{4}P_L^2\right)$$

by reinserting $$\frac{P_L}{P_1-P_2}$$

for $K_p$ and, as in Eq. (5), $$\left.\frac{dP}{dt}\right|_{P=P_L/2} \text{ for } \frac{P_1-P_2}{t_m}.$$

Equation (11) can be simplified to:

$$\frac{\omega_t}{\omega_m} = K_{qf_t}t_m(1+C_f)$$

where $K_x$ is a constant equal to $$\frac{K_p}{K_t V}$$

and $C_f$ is a correction factor dependent on pipeline gas pressure, temperature, and composition. The second term $$\frac{(b^2-c)}{4} P_L^2$$

in Eq. (11) is an error correction term and is significant at high pressures. For methane gas, b is about 0.0024 and c is about $3.1\times10^{-6}$ when pressure is measured in bars. If $P_L$ is 30 bar (i.e. 440 psia), the error associated with the second term is about 0.25%.

The error associated by the second term $$\frac{(b^2-c)}{4} P_L^2$$

in Eq. (11) can be reduced by determining values for b and c. It is convenient to rewrite the second term $$\frac{(b^2-c)}{4} P_L^2$$

in terms of the third density virial coefficient C:

$$\frac{(b^2-c)}{4} P_L^2 = \left(2b^2 - \frac{C}{(RT)^2}\right)\frac{P_L^2}{4} \tag{12}$$

The value of b can be determined by a second measurement at low absolute pressure. For low absolute pressure, the total derivative of pressure with respect to time $$\left(\frac{dP}{dt}\right)_T$$

can be written in the form of Eq. (4) but neglecting the third viral coefficient c:

$$\left(\frac{dP}{dt}\right)_T = \frac{RT(1+2bP_{Y1})}{M_w V}\,\omega_m \tag{13}$$

where $P_{Y1}$ is a low pressure. The sample gas 18 mass flow rates $\omega_m$ in Eqs. (4) and (13) are the same as selected by the flow controller 26. The second virial coefficient b can be estimated by combining and simplifying Eqs. (4) and (13):

$$b = \frac{\dot{P}_1 - \dot{P}_{Y1}}{2(P_1\dot{P}_{Y1} - P_{Y1}\dot{P}_1)} \tag{14}$$

where $\dot{P}_1$ is the total pressure derivative at $P_1$ and $\dot{P}_{Y1}$ is the total pressure derivative at low pressure. Equation (14) can be expressed in terms of pressures and time interval measurements:

$$b = \frac{\frac{P_1-P_2}{t_m} - \frac{P_{Y1}-P_{Y2}}{t_Y}}{2\left(P_1\frac{P_{Y1}-P_{Y2}}{t_Y} - P_{Y1}\frac{P_1-P_2}{t_m}\right)} \tag{15}$$

where $t_Y$ is the time interval for a pressure decay at low pressure (i.e. $P_{Y1}$-$P_{Y2}$) and is determined in a manner similar to the internal $t_m$. There is no requirement that $P_{Y1}$ or $P_{Y2}$ be a specific pressure other than $P_{Y2}$ be less than $P_{Y1}$.

Equations (14) and (15) assume that the volume in which the pressure drops $P_1$-$P_2$ and $P_{Y1}$-$P_{Y2}$ occur is constant. This assumption is true if the pressure drops are both measured in the first chamber 20 (or in the first section 43 of the hollow coil 20' if the embodiment shown in FIG. 3 is used), but at different times.

Figure 5:
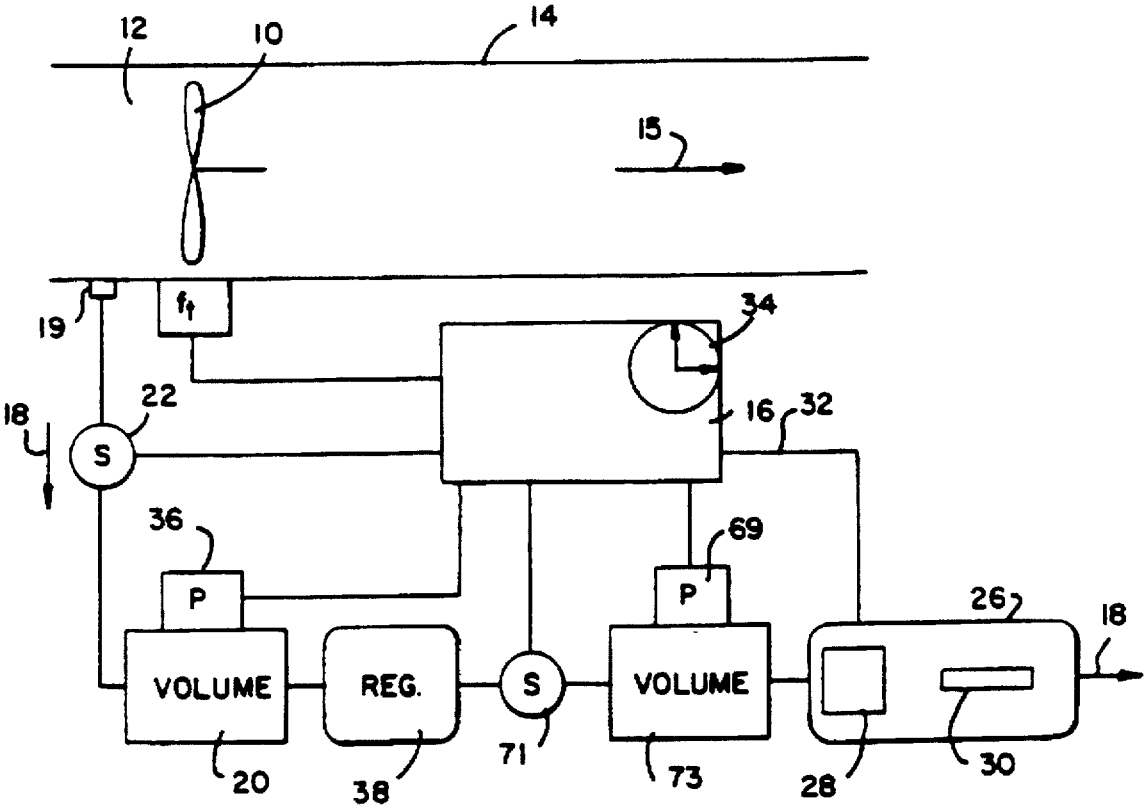
FIG. 5 is a schematic drawing showing an embodiment of the present invention in which a second chamber is located in-line between a pressure regulator and a flow controller.

Referring to FIG. 5, it may be preferable in some circumstances to use a second fixed-volume chamber 73 downstream of the first chamber 20 and measure the low pressure drop ($P_{Y1}$-$P_{Y2}$) in the second chamber 73. In FIG. 5, the sample gas 18 pressure is reduced significantly as the sample gas 18 flows from the first chamber 20 to the second chamber 73 by an in-line pressure regulator 38. A third solenoid valve 71 is located in line between the pressure regulator 38 and the second chamber 73. A pressure sensor 69 measures the sample gas pressure in the second chamber 73. The timer 34 measures the time interval $t_Y$ for the pressure to decay from $P_{Y1}$ to $P_{Y2}$ in the second chamber 73. An advantage of the of configuration shown in FIG. 5 is a reduction in waiting time for the sample gas pressure to decay to the low pressure $P_{Y1}$. If the configuration shown in FIG. 5 is used and the volume of the second chamber 73 is different than the volume of the first chamber 20 (or the volume of the first section 43 of the hollow coil 20' if the embodiment shown in FIG. 3 is used), Eqs. (14) and (15) should be replaced with:

$$b = \frac{V\dot{P}_1 - V_Y\dot{P}_{Y1}}{2(P_1V_Y\dot{P}_{Y1} - P_{Y1}V\dot{P}_1)} \tag{16}$$

and:

$$b = \frac{V\frac{P_1-P_2}{t_m} - V_Y\frac{P_{Y1}-P_{Y2}}{t_Y}}{2\left(P_1V_Y\frac{P_{Y1}-P_{Y2}}{t_Y} - P_{Y1}V\frac{P_1P_2}{t_m}\right)} \tag{15}$$

where V is the volume of the first chamber 20 (or the volume of the first section 43 of the hollow coil 20' if the embodiment shown in FIG. 3 is used) and $V_Y$ is the volume of the second chamber 73.

For the natural gas, which usually consists of 80% or more natural gas, the value of $$\frac{C}{4\,(RT)^2}$$

in Eq. (12) can be approximated by a relationship in the form of $KP^2$ where K is a constant and P is pressure. In Table 1 are listed values of c and of $$\frac{C}{4\,(RT)^2}$$

for pure methane and also for mixtures containing 80% methane each at 45° F. and 81° F. The values in Table 1 were obtained from published data, such as the Brugge Data from Texas A&M, and from interpolating the published data using thermodynamic mixing rules for virial coefficients.

TABLE 1

| Mixture | c @280° K. $cm^6/mol^2$ | c @300° K. $cm^6/mol^2$ | $C/4(RT)^2$ @280° K. $10^6$ $acm^{-2}$ | $C/4(RT)^2$ @300° K. $10^6$ $acm^{-2}$ |
|---|---|---|---|---|
| Methane ($CH_4$) | 2649 | 2438 | 1.256 | 1.007 |
| Ethane ($C_2H_6$) | 10774 | 10392 | | |
| 80% $CH_4$; 20% $C_2H_6$ | 3714 | 3463 | 1.761 | 1.431 |

TABLE 1-continued

| Mixture | c @280° K. $cm^6/mol^2$ | c @300° K. $cm^6/mol^2$ | $C/4(RT)^2$ @280° K. $10^6$ $acm^{-2}$ | $C/4(RT)^2$ @300° K. $10^6$ $acm^{-2}$ |
|---|---|---|---|---|
| Carbon Dioxide ($CO_2$) | 5636 | 4927 | | |
| 80% $CH_4$; 20% ($CO_2$) | 3130 | 2844 | 1.484 | 1.175 |
| Nitrogen ($N_2$) | 1451 | 1443 | | |
| 80% $CH_4$; 20% $N_2$ | 2371 | 2211 | 1.124 | 0.913 |

The splitting ratio $$S = \frac{\omega_t}{\omega_m}$$

is computed in real time by the control system 16 in accordance with Eq. (11). In the calculation, $K_P$, $K_t$, and V are constants stored within the control system 16 and the turbine frequency $f_t$, and the time interval $t_m$ are communicated to the control system 16 for each sampling cycle 24. The second virial coefficient b is estimated by measuring the time interval $t_Y$ for a pressure decay at low pressure and using Eq. (15) or (17), whichever is appropriate. The third virial coefficient c is estimated using data from Table 1. Finally, $P_L$ is measured by the pressure sensor 36 and relayed to the control system 16.

Figure 6:
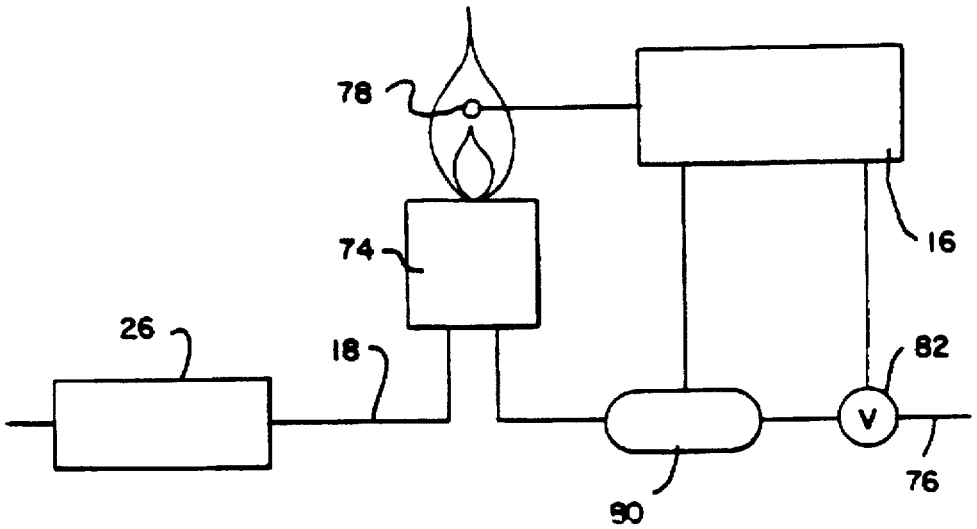
FIG. 6 is a schematic drawing showing additional apparatus of the present invention for measuring the energy flow rate of a pipeline gas through a pipeline.

Referring generally to FIG. 6, the method and apparatus described above can be used with the method and apparatus described hereafter, which is much like the method and apparatus for determining the energy content of the flow of pipeline gas that is described in U.S. Pat. No. 4,125,123 issued to Clingman on Nov. 14, 1978.

For saturated hydrocarbon gas, the amount of air required to completely combust gas at maximum flame temperature, i.e. stoichiometric combustion, is precisely proportional to the energy released during combustion. If the gas being combusted is a saturated hydrocarbon, the energy flow rate of the sample gas 18 is represented by:

$$\frac{\delta E_t}{\delta t} = K_{sto}\omega_{air} \tag{18}$$

where $K_{sto}$ is the stoichiometric proportionalit$_Y$ constant, and $\omega_{air}$ is the air flow rate. Likewise, the energy flow rate of the gas 12 through the pipeline 14 is represented by:

$$\frac{\delta E_t}{\delta t} = S\,K_{th}\omega_{air} = K_{th}\omega_{air}\frac{K_p f_t t_m}{K_t V}\left(1 + \frac{(b^2 - c)}{4}\,P_L^2\right) \tag{19}$$

where S is the splitting ratio as defined in Eq. (11).

Equation (19) can be simplified to:

$$\frac{\delta E_t}{\delta t} = K_x f_t t_m \omega_{air}(1 + C_f)$$

where $K_x$ is a constant equal to $$\frac{K_p}{K_t V}$$

and $C_f$ is a correction factor dependent on pipeline gas pressure, temperature, and composition.

In accordance with Eq. 19, the apparatus shown in FIG. 6 determines the energy flow rate of the pipeline gas 12 through the pipeline 14.

Referring in particular to FIG. 6, the sample gas 18 flows to a burner 74 at a flow rate maintained by the flow controller 26. Air is supplied to the burner 74 by an air hose 76 and the sample gas 18 is burned above the burner 74. A temperature sensor 78, which communicates to the control system 16, monitors flame temperature. The air flowing through the air hose 76 is monitored by an air mass flow meter 80. Air mass flow meters are old in the art and are accurate at ambient conditions. The air flow is adjusted by an air valve 82, which also communicates with the control system 16, until the sample gas 18 burns at maximum flame temperature. When the flame burns at the maximum flame temperature, the energy flow rate of the pipeline gas 12 can be determined.

The energy flow rate of the pipeline gas 12 is calculated in the control system 16 in accordance with Eq. (19). The value $K_{sto}$ in Eq. (19) is a constant and stored in the control system 16. The splitting ratio S is computed for each sampling cycle 24 as described above. And, the air mass flow rate $\omega_{air}$ is measured by the air flow meter 80 and communicated to the control system 16 for each sampling cycle 24.

U.S. Pat. No. 4,125,123 issued to Clingman discloses a method for determining the energy content (energy/volume) of a pipeline gas at standard operating conditions. It is well known in the art that the volumetric flow rate adjusted for standard operating conditions can be determined by dividing energy flow rate (energy/time) by energy content (energy/volume).

Many modifications and variations of the preferred embodiment that are within the spirit and scope of the invention will be apparent to those with ordinary skill in the art.

We claim:

1. An apparatus to be used with a linear flow meter to measure a ratio of a mass flow rate of a pipeline gas through a pipeline compared to a mass flow rate of a sample gas tapped from the pipeline, the apparatus comprising:

a chamber having a section with a fixed volume for containing the sample gas, the sample gas being maintained at substantially the same temperature as the pipeline gas in the pipeline when contained in the chamber section;

means for routing the sample gas to the chamber section;

a valve for controlling the flow of sample gas to the chamber section;

a flow controller for flowing the sample gas from the chamber section at a selected rate;

a pressure sensor for measuring the sample gas pressure in the chamber section;

means for closing the valve when the sample gas pressure in the chamber section reaches the pressure of the pipeline gas in the pipeline; and a timer for measuring a time interval for the sample gas to flow from the chamber section at the selected rate beginning when the sample gas pressure in the chamber section drops below a first pressure, and ending when the sample gas pressure in the chamber section drops below a second pressure, the first pressure being greater than about one-half of the pipeline gas pressure in the pipeline and the second pressure being less than about one-half of the pipeline gas pressure in the pipeline; and a controller which receives a signal from the timer and a signal from the linear flow meter representing the volumetric flow of the pipeline gas through the pipeline and derives the ratio of the mass flow rate of the pipeline gas through the pipeline compared to the mass flow rate of the sample gas.

2. An apparatus as recited in claim 1 further comprising means for quickly reducing the sample gas pressure in the chamber section from the pipeline gas pressure to the first pressure.

3. An apparatus as recited in claim 2 wherein the means for quickly reducing the sample gas pressure in the chamber section from the pipeline gas pressure to the first pressure comprises a second section in the chamber.

4. An apparatus as recited in claim 1 further comprising a pressure regulator for reducing the pressure of the sample gas before the sample gas flows to the flow controller.

5. An apparatus as recited in claim 1 wherein the controller calculates the mass flow ratio in accordance with the following function:

$$\frac{\omega_t}{\omega_m} = K_x f_t t_m (1 + C_f),$$

where $K_x$ is a constant, $f_t$ is a signal from linear flow meter, $t_m$ is the time interval and $C_f$ is a correction factor dependent on the pipeline gas pressure, temperature and composition.

6. An apparatus as recited in claim 5 further comprising a second chamber located such that the sample gas flows through the second chamber before it flows to the flow controller.

7. An apparatus to be used with a linear flow meter for measuring the energy flow rate of a pipeline gas through a pipeline, the apparatus comprising:

a chamber having a section with a fixed volume for containing the sample gas, the sample gas being maintained at substantially the same temperature as the pipeline gas in the pipeline when contained in the chamber section;

means for routing the sample gas to the chamber section;

a valve for controlling the flow of sample gas to the chamber section;

a flow controller for flowing the sample gas from the chamber section at a selected rate;

a pressure sensor for measuring the sample gas pressure in the chamber section;

means for closing the valve when the sample gas pressure in the chamber section reaches the pressure of the pipeline gas in the pipeline;

a timer for measuring a time interval for the sample gas to flow from the chamber section at the selected rate beginning when the sample gas pressure in the chamber section drops below a first pressure, and ending when the sample gas pressure in the chamber section drops below a second pressure, the first pressure being greater than about one-half of the pipeline gas pressure in the pipeline and the second pressure being less than about one-half of the pipeline gas pressure in the pipeline;

a sample gas energy flow rate meter for measuring the energy flow rate of the sample gas; and a controller which receives a signal from the timer, the linear flow meter which represents the volumetric flow of the pipeline gas through the pipeline the sample gas energy flow rate meter and derives the energy flow rate of the pipeline gas through this pipeline.

8. An apparatus as recited in claim 7 wherein the sample gas energy flow rate meter comprises:

a burner for burning the sample gas with air to form a flame; and means for maximizing the flame temperature.

9. An apparatus as recited in claim 8 further comprising an air mass flow meter for measuring the air mass flow rate of the air burning the sample gas.

10. An apparatus as recited in claim 9 wherein the controller calculates the energy flow rate in accordance with the following function:

$$\frac{\delta E_t}{\delta t} = K_x f_t t_m \omega_{air} (1 + C_f),$$

where $K_x$ is a constant, $f_t$ is a signal from the linear flow meter, $t_m$ is the time interval, $\omega_{air}$ is the air mass flow rate and $C_f$ is a correction factor dependent on the pipeline gas pressure, temperature, and composition.

11. A method for measuring a mass flow ratio $$\left(\frac{\omega_t}{\omega_m}\right)$$

of a pipeline gas through a pipeline compared to a sample gas tapped from the pipeline, the method comprising the steps of:

measuring the volumetric flow rate of the pipeline gas through the pipeline with a linear flow meter;

flowing the sample gas to a chamber having a section with a fixed volume;

maintaining the temperature of the sample gas at substantially the same temperature as the pipeline gas in the pipeline when the sample gas is in the chamber section;

stopping the flow of sample gas to the chamber section when the pressure in the chamber section reaches the pressure of the pipeline gas in the pipeline;

flowing the sample gas from the chamber section after the flow of the sample gas to the chamber section is stopped, thereby reducing the sample gas pressure in the chamber section;

timing the interval of time $t_m$ for the sample gas to flow from the chamber section at a selected rate beginning when the sample gas pressure in the chamber section drops below a first pressure and ending when the sample gas pressure in the chamber section drops below a second pressure wherein the first pressure is greater than about one-half of the pipeline gas pressure in the pipeline and the second pressure is less than about one-half of the pipeline gas pressure in the pipeline; and deriving the mass flow ratio $$\left(\frac{\omega_t}{\omega_m}\right)$$

of the pipeline gas through the pipeline compared to the sample gas tapped from the pipeline from a signal $f_t$ from the linear flow meter that is related to the volumetric flow rate of the pipeline gas, and the time interval $t_m$.

12. A method as recited in claim 11 wherein the mass flow ratio is derived in a control system.

13. A method as recited in claim 12 wherein the control system calculates the mass flow ratio in accordance with the following function:

$$\frac{\omega_t}{\omega_m} = K_x f_t t_m (1 + C_f),$$

where $K_x$ is a constant, $f_t$ is a signal from the linear flow meter, $t_m$ is the time interval and $C_f$ is a correction factor dependent on the pipeline gas pressure, temperature and composition.

14. A method as in claim 13 further comprising the steps of:

flowing the sample gas to a second chamber of fixed volume;

stopping the flow of sample gas to the second chamber when the pressure of the sample gas in the second chamber is greater than or equal to a third pressure;

flowing the sample gas from the second chamber after the flow of the sample gas to the second chamber is stopped, thereby reducing the sample gas pressure in the second chamber;

timing the interval of time for the sample gas to flow from the second chamber at the selected rate beginning when the sample gas pressure in the second chamber drops below a third pressure and ending when the sample gas pressure in the second chamber section drops below a fourth pressure; and determining a value for the correction factor $C_f$ in accordance with the following function:

$$\frac{(b^2 - c)}{4} P_L^2$$

where $P_L$ is the pipeline gas pressure, c is estimated using data stored in the control system and b is estimated in accordance with the following function:

$$b = \frac{V_1 \frac{P_1 - P_2}{t_m} - V_2 \frac{P_3 - P_4}{t_Y}}{2\left(P_1 V_2 \frac{P_3 - P_4}{t_Y} - P_3 V_1 \frac{P_1 - P_2}{t_m}\right)}$$

where $V_1$ is the volume of the chamber section, $V_2$ is the volume of the second chamber, $P_1$ is the first pressure, $P_2$ is the second pressure, $P_3$ is the third pressure, $P_4$ is the fourth pressure, $t_m$ is the time interval for the pressure in the chamber section to drop from $P_1$ to $P_2$, and $t_Y$ is the time interval for the pressure in the second chamber to drop from $P_3$ to $P_4$.

15. A method for measuring the energy flow rate of a pipeline gas through a pipeline, the method comprising:

measuring the volumetric flow rate of the pipeline gas through the pipeline with a linear flow meter;

flowing the sample gas to a chamber having a section with a fixed volume;

maintaining the temperature of the sample gas at substantially the same temperature as the pipeline gas in the pipeline when the sample gas is in the chamber section;

stopping the flow of sample gas to the chamber section when the pressure in the chamber section reaches the pressure of the pipeline gas in the pipeline;

flowing sample gas from the chamber section at a selected rate after the flow of sample gas to the chamber section is stopped, thereby reducing the sample gas pressure in the chamber section;

timing the interval of time $t_m$ for the sample gas to flow from the chamber section at a selected rate beginning when the sample gas pressure in the chamber section drops below a first pressure and ending when the sample gas pressure in the chamber section drops below a second pressure wherein the first pressure is greater than about one-half of the pipeline gas pressure in the pipeline and the second pressure is less than about one-half of the pipeline gas pressure in the pipeline;

measuring the energy flow rate of the sample gas; and determining the energy flow rate of the pipeline gas through the pipeline from a signal $f_t$ from the linear flow meter that is related to the volumetric flow rate of the pipeline gas, the time interval $t_m$, and the energy flow rate of the sample gas.

16. A method as recited in claim 15 wherein the energy flow rate of the sample gas is measured by:

burning the sample gas flowing from the chamber with air; and adjusting the air flow so that the sample gas burns at maximum flame temperature.

17. A method as recited in claim 15 wherein the energy flow rate of the pipeline gas is determined in a control system.

18. A method as recited in claim 17 further comprising the step of measuring the air mass flow rate of air burning the sample gas.

19. A method as recited in claim 18 wherein the control system calculates the energy flow rate in accordance with the following function:

$$\frac{\delta E_t}{\delta_t} = K_x f_t t_m \omega_{air} (1 + C_f),$$

where $K_x$ is a constant, $f_t$ is a signal form the linear flow meter, $t_m$ is the time interval, $\omega_{air}$ is the air mass flow rate and $C_f$ is a correction factor dependent on the pipeline gas pressure, temperature and composition.

20. A method as recited in claim 19 further comprising the steps of:

flowing the sample gas to a second chamber of fixed volume;

stopping the flow of sample gas to the second chamber when the pressure of the sample gas in the second chamber is greater than or equal to a third pressure;

flowing the sample gas from the second chamber after the flow of the sample gas to the second chamber is stopped, thereby reducing the sample gas pressure in the second chamber;

timing the interval of time for the sample gas to flow from the second chamber at the selected rate beginning when the sample gas pressure in the second chamber drops below a third pressure and ending when the sample gas pressure in the second chamber section drops below a forth pressure; and determining a value for the correction factor $C_f$ in accordance with the following function:

$$\frac{(b^2 - c)}{4} P_L^2$$

where $P_L$ is the pipeline gas pressure, c is estimated using data stored in the control system and b is estimated in accordance with the following function:

$$b = \frac{V_1 \frac{P_1 - P_2}{t_m} - V_2 \frac{P_3 - P_4}{t_Y}}{2\left(P_1 V_2 \frac{P_3 - P_4}{t_Y} - P_3 V_1 \frac{P_1 - P_2}{t_m}\right)}$$

where $V_1$ is the volume of the chamber section, $V_2$ is the volume of the second chamber, $P_1$ is the first pressure, $P_2$ is the second pressure, $P_3$ is the third pressure, $P_4$ is the fourth pressure, $t_m$ is the time interval for the pressure in the chamber section to drop from $P_1$ to $P_2$, and $t_Y$ is the time interval for the pressure in the second chamber to drop from $P_3$ to $P_4$.

21. An apparatus that measures a ratio of a mass flow rate of a pipeline gas through a pipeline compared to a mass flow rate of a sample gas tapped from the pipeline for use with a linear flow meter measuring the volumetric flow of the pipeline gas through the pipeline, the apparatus comprising:

a chamber having a section with a fixed volume for containing the sample gas, the sample gas being maintained at substantially the same temperature as the pipeline gas in the pipeline when contained in the chamber section;

a pressure sensor for measuring the pressure of the sample gas in the chamber section;

a first line connected to the pipeline for routing the sample gas to the chamber section;

a valve mounted in the first line for controlling the flow of the sample gas to the chamber section;

a flow controller for flowing the sample gas from the chamber at a selected rate;

a second line for routing the sample gas away from the chamber to the flow controller;

a control for closing the valve when the sample gas pressure in the chamber section reaches the pressure of the pipeline gas in the pipeline;

a timer for measuring a time interval for the sample gas to flow from the chamber section at the selected rate beginning when the sample gas pressure in the chamber section drops below a first pressure, and ending when the sample gas pressure in the chamber section drops below a second pressure, the first pressure being greater than about one-half of the pipeline gas pressure in the pipeline and the second pressure being less than about one-half of the pipeline gas pressure in the pipeline;

a third line for routing the sample gas away from the flow controller; and a control system for receiving signals from the pressure sensor, the timer and the linear flow meter and for computing the ratio of the mass flow rate of the pipeline gas through the pipeline compared to the mass flow rate of the sample gas.

22. An apparatus as recited in claim 21 further comprising a second chamber of fixed volume located in the second line so that the sample gas flows through the second chamber before it flows to the flow controller.

23. An apparatus as recited in claim 22 further comprising a pressure regulator located in the second line for reducing the sample gas pressure before the sample gas flows to the second chamber.

24. An apparatus as recited in claim 21 wherein the chamber has a second section located downstream of the chamber section with the fixed-volume and further comprising a second valve for controlling the flow of the sample gas from the fixed-volume chamber section to the second chamber section.

25. An apparatus for measuring the energy flow rate of a pipeline gas through a pipeline, the apparatus to be used with a linear flow meter measuring the volumetric flow of the pipeline gas through the pipeline, the apparatus comprising:

a chamber having a section with a fixed volume for containing the sample gas, the sample gas being maintained at substantially the same temperature as the pipeline gas in the pipeline when contained in the chamber section;

a pressure sensor for measuring the pressure of the sample gas in the chamber section;

a first line connected to the pipeline for routing the sample gas to the chamber section;

a valve mounted in the first line for controlling the flow of the sample gas to the chamber section;

a flow controller for flowing the sample gas from the chamber at a selected rate;

a second line for routing the sample gas away from the chamber to the flow controller;

a control for closing the valve when the sample gas pressure in the chamber section reaches the pressure of the pipeline gas in the pipeline;

a timer for measuring a time interval for the sample gas to flow from the chamber section at the selected rate beginning when the sample gas pressure in the chamber section drops below a first pressure, and ending when the sample gas pressure in the chamber section drops below a second pressure, the first pressure being greater than about one-half of the pipeline gas pressure in the pipeline and the second pressure being less than about one-half of the pipeline gas pressure in the pipeline;

a burner for burning the sample gas with an air flow to form a flame;

a third line for routing the sample gas away from the flow controller to the burner;

a temperature sensor for measuring the flame temperature;

an air conduit for routing the air flow to the burner;

an air valve located in the air conduit for adjusting the air flow through the air conduit;

an air mass flow meter for measuring an air mass flow rate through the air conduit; and a control system for receiving signals from the pressure sensor, the timer, the linear flow meter, the air mass flow meter and the temperature sensor, for communicating with the air valve to adjust the air flow so that the flame burns at the maximum temperature, and for computing the energy flow rate of the pipeline gas flowing through the pipeline.

26. An apparatus as recited in claim 25 further comprising a second chamber of fixed volume located in the second line so that the sample gas flows through the second chamber before it flows to the flow controller.

27. An apparatus as recited in claim 26 further comprising a pressure regulator located in the second line for reducing the sample gas pressure before the sample gas flows to the second chamber.

28. An apparatus as recited in claim 25 wherein the chamber has a second section located downstream of the chamber section with the fixed-volume and further comprising a second valve for controlling the flow of the sample gas from the fixed-volume chamber section to the second chamber section.

29. An apparatus to be used with a linear flow meter to measure a ratio of a mass flow rate of a pipeline gas through a pipeline compared to a mass flow rate of a sample gas tapped from the pipeline, the apparatus comprising:

a chamber having a section with a fixed volume V for containing the sample gas, the sample gas being maintained at substantially the same temperature as the pipeline gas in the pipeline when contained in the chamber section;

means for routing the sample gas to the chamber section;

a valve for controlling the flow of sample gas to the chamber section;

a flow controller for flowing the sample gas from the chamber section at a selected rate;

a pressure sensor for measuring the sample gas pressure in the chamber section;

means for closing the valve when the sample gas pressure in the chamber section reaches the pressure $P_L$ of the pipeline gas in the pipeline; and means for determining a time rate of change of pressure in the chamber section for a condition where the pressure in the chamber section is about one-half of pressure $P_L$ of the pipeline gas in the pipeline $$\left(\frac{dP}{dt}\bigg|_{P=P_L/2}\right);$$

a control system which receives a signal $f_t$ representing volumetric flow through the pipeline from the linear flow meter, and signals from the pressure sensor, and computes the ratio $$\left(\frac{\omega_t}{\omega_m}\right)$$

of the mass flow rate of the pipeline gas through the pipeline compared to the mass flow rate of the sample gas by the following relationship:

$$\frac{\omega_t}{\omega_m}=\frac{P_L f_t}{K_t V}\left(\frac{dP}{dt}\bigg|_{P=L/2}\right)^{-1}\left(1+\frac{(b^2-c)}{4}P_L^2\right)$$

where $K_t$ is a calibration constant for the linear flow meter, b is a second pressure virial coefficient of the gas and c is a third pressure virial coefficient of the gas.

30. A method for measuring a mass flow ratio $$\left(\frac{\omega_t}{\omega_m}\right)$$

of a pipeline gas through a pipeline compared to a sample gas tapped from the pipeline, the method comprising the steps of:

measuring the volumetric flow rate of the pipeline gas through the pipeline with a linear flow meter;

flowing the sample gas to a chamber having a section with a fixed volume V;

maintaining the temperature of the sample gas at substantially the same temperature as the pipeline gas in the pipeline when the sample gas is in the chamber section;

stopping the flow of sample gas to the chamber section when the pressure in the chamber section reaches the pressure $P_L$ of the pipeline gas in the pipeline;

flowing the sample gas from the chamber section after the flow of the sample gas to the chamber section is stopped, thereby reducing the sample gas pressure in the chamber section;

determining the time rate of change of pressure in the chamber section for a condition where the pressure in the chamber section in about one-half of pressure $P_L$ of the pipeline gas in the pipeline $$\left(\frac{dP}{dt}\bigg|_{P=P_{L/2}}\right)$$

and deriving the mass flow ratio $$\left(\frac{\omega_t}{\omega_m}\right)$$

of the pipeline gas through the pipeline compared to the sample gas tapped from the pipeline by solving the following relationship:

$$\frac{\omega_t}{\omega_m}=\frac{P_L f_t}{K_t V}\left(\frac{dP}{dt}\bigg|_{P=L/2}\right)^{-1}\left(1+\frac{(b^2-c)}{4}P_L^2\right)$$

where $f_t$ is a signal from the linear flow meter representing the volumetric flow rate of the gas through the pipeline, $K_t$ is a calibration constant for the linear flow meter, b is a second virial coefficient of the gas, and c is a third virial coefficient of the gas.

31. A method for monitoring the energy flow rate of a pipeline gas through a pipeline and representing the flow of the pipeline gas in terms of an adjusted volumetric flow rate which corresponds to a volumetric flow rate at a defined pressure and temperature, the method comprising:

measuring the volumetric flow rate of the pipeline gas through the pipeline with a linear flow meter;

flowing sample gas to a chamber having a section with a fixed volume;

maintaining the temperature of the sample gas at substantially the same temperature as the pipeline gas in the pipeline when the sample gas is in the chamber section;

stopping the flow of sample gas to the chamber section when the pressure in the chamber section reaches the pressure of the pipeline gas in the pipeline;

flowing sample gas from the chamber section at a selected rate after the flow of sample gas to the chamber section is stopped, thereby reducing the sample gas pressure in the chamber section;

timing the interval of time $t_m$ for the sample gas to flow from the chamber section at a selected rate beginning when the sample gas pressure in the chamber section drops below the first pressure and ending when the sample gas pressure in the chamber section drops below a second pressure;

measuring the energy flow rate of the sample gas;

measuring the energy content per unit volume of the sample gas; and determining the adjusted volumetric flow rate of the pipeline gas through the pipeline from the volumetric flow rate of the pipeline gas measured by the linear meter, the time interval $t_m$, the energy flow rate of the sample gas, and the energy content per unit volume of the sample gas.

32. An apparatus to be used with a control system and a linear flow meter measuring a volumetric flow rate of a pipeline gas flowing through a pipeline, for monitoring the energy flow rate of the pipeline gas through the pipeline and representing the flow of the pipeline gas in terms of an adjusted volumetric flow rate that corresponds to a volumetric flow rate at a defined pressure and temperature, the apparatus comprising:

a chamber having a section with a fixed volume for containing the sample gas, the sample gas being maintained at substantially the same temperature as the pipeline gas in the pipeline when contained in the chamber section;

means for routing the sample gas to the chamber section;

a valve for controlling the flow of sample gas to the chamber section;

a flow controller for flowing the sample gas from the chamber section at a selected rate;

a pressure sensor for measuring the sample gas pressure in the chamber section;

means for closing the valve when the sample gas pressure in the chamber section reaches the pressure of the pipeline gas in the pipeline;

a timer for measuring a time interval for the sample gas to flow from the chamber section at the selected rate beginning when the sample gas pressure in the chamber section drops below a first pressure and ending when the sample gas pressure in the chamber section drops below a second pressure;

a sample gas energy flow rate meter for measuring the energy flow rate of the sample gas; and means for determining the energy content per unit volume of the sample gas;

wherein the control system calculates the adjusted volumetric flow rate of the pipeline gas through the pipeline from the volumetric flow rate measured by the linear flow meter, the time interval, the energy flow rate of the sample gas, and the energy content per unit volume of the sample gas.

33. An apparatus to be used with a linear flow meter to measure a ratio of a mass flow rate of a pipeline gas through a pipeline compared to a mass flow rate of a sample gas tapped from the pipeline, the apparatus comprising:

a chamber having a section with a fixed volume for containing the sample gas, the sample gas being maintained at substantially the same temperature as the pipeline gas in the pipeline when contained in the chamber section;

means for routing the sample gas to the chamber section;

a valve for controlling the flow of sample gas to the chamber section;

a flow controller for flowing the sample gas from the chamber section at a selected rate;

a pressure sensor for measuring the sample gas pressure in the chamber section;

means for closing the valve when the sample gas pressure in the chamber section reaches the pressure of the pipeline gas in the pipeline; and a timer for measuring a time interval for the sample gas to flow from the chamber section at the selected rate beginning when the sample gas pressure in the chamber section drops below a first pressure, and ending when the sample gas pressure in the chamber section drops below a second pressure, the first pressure being equal to one-half of the pipeline gas pressure in the pipeline and the second pressure being less than the first pressure; and a controller which receives a signal from the timer and a signal from the linear flow meter representing the volumetric flow of the pipeline gas through the pipeline and derives the ratio of the mass flow rate of the pipeline gas through the pipeline compared to the mass flow rate of the sample gas.

*34. An apparatus to be used with a flow meter that generates a signal representing flow rate of gas in a pipeline, said apparatus measuring a ratio of a mass flow rate of the gas in the pipeline to a mass flow rate of a sample gas tapped from the pipeline, the apparatus comprising:*

*a chamber having a known volume for receiving the sample gas, the sample gas being maintained at substantially the same temperature as the pipeline gas;*

*means for controlling the flow of the sample gas from said chamber, said means generating at least one signal indicative of mass flow rate of the sample gas; and*

*a controller which receives the signal from the flow meter and at least one signal from the means for controlling the flow of the sample gas, said controller being operable in response thereto, to calculate the ratio of the mass flow rate of the gas through the pipeline to the mass flow rate of the sample gas.*

*35. An apparatus as recited in claim 34, further comprising means for reducing the sample gas pressure in the chamber from a pipeline gas pressure to a pressure for measuring mass flow rate of the sample gas.*

*36. An apparatus as recited in claim 35, wherein the means for reducing the sample gas pressure comprises a second chamber communicating with said first-mentioned chamber.*

*37. An apparatus as recited in claim 36, further comprising a pressure regulator in a path of flow between the first-mentioned chamber and the second chamber for reducing the pressure of the sample gas before the sample gas flows to a flow controller.*

*38. An apparatus as recited in claim 34, wherein the gas in the pipeline is at pipeline pressure, and wherein the means for controlling the flow of the sample gas generates at least one signal indicative of a time interval in response to a decrease in pressure of the sample gas in the chamber from a first predetermined pressure to a second predetermined pressure, wherein said first predetermined pressure is greater than one-half of the pipeline pressure and wherein said second predetermined pressure is less than one-half of the pipeline pressure.*

*39. A method for measuring the energy flow of a gas through a pipeline, the method comprising:*

*measuring the volumetric flow rate of gas through the pipeline;*

*capturing in a chamber of predetermined volume, a sample of the gas in the pipeline at substantially the same temperature and pressure as the gas in the pipeline;*

*measuring the energy contained in the sample of the gas in the chamber of predetermined volume;*

*calculating the energy flow of gas in the pipeline in response to the volumetric flow rate of pipeline gas in the pipeline, and in response to the energy measured in the sample of the gas from the pipeline.*

*40. The method of claim 39, wherein the step of measuring the volumetric flow rate of gas through the pipeline further comprises:*

*measuring a ratio of the mass flow rate of gas in the pipeline to the mass flow rate of the sample of gas in the chamber of predetermined volume by:*

*flowing at least a portion of the sample of gas out of the chamber of predetermined volume; and*

*measuring a time interval ($t_m$) corresponding to a predetermined pressure change, said pressure change resulting from the flowing of the portion of the sample of gas out of the chamber.*

*41. The method of claim 39, wherein the step of measuring the volumetric flow rate of gas through the pipeline further comprises measuring a signal ($f_t$) from a turbine flow meter in the pipeline and multiplying by a constant ($K_t$) to determine the volumetric flow rate of the pipeline gas in the pipeline.*

*42. The method of claim 41, wherein the step of measuring the energy contained in the sample of gas includes the step of measuring the volume of air required to combust the sample of gas at a maximum flame temperature.*

*43. The method of claim 39, wherein the step of measuring the energy contained in the sample of the gas in the chamber of predetermined volume further includes measuring the energy flow rate of the sample of gas flowed out of the chamber of predetermined volume.*

*44. The claim of claim 43, wherein the step of measuring the energy flow rate of the sample of gas further includes the steps of:*

*burning said sample of the gas with air; and*

*adjusting the flow of the air to obtain maximum flame temperature; and*

*measuring the flow rate of air ($\omega_{air}$) at maximum flame temperature.*

*45. The method of claim 44, wherein the step of measuring volumetric flow rate further comprises:*

*measuring a ratio of the mass flow rate of gas in the pipeline to the mass flow rate of the sample of gas in the chamber of predetermined volume by:*

*flowing at least a portion of the sample of gas out of the chamber of predetermined volume; and*

*measuring a time interval ($t_m$) corresponding to a predetermined pressure change, said predetermined pressure change resulting from the flowing of the portion of the sample of gas out of the chamber.*

*46. The method of claim 45, wherein the step of measuring the volumetric flow rate of the pipeline gas further comprises the step of adjusting the volumetric flow rate of the pipeline gas to standard operating conditions in response to the ratio of the mass flow rates, and in response to the flow rate of air ($\omega_{air}$) at maximum flame temperature.*

*47. Apparatus for measuring the energy flow of a gas through a pipeline, the apparatus comprising:*

*a pipeline flow meter that measures the volumetric flow rate of gas through the pipeline and generates a signal indicative thereof;*

*means including a chamber of predetermined volume for receiving a sample of the gas in the pipeline at substantially the same temperature as the gas in the pipeline;*

*means for combusting the sample of the gas from the chamber of predetermined volume and generating a signal indicative of energy content of said sample of gas;*

*wherein said chamber receives successive samples of gas and wherein said samples are combusted by said means for combusting; and*

*means responsive to the signals from the pipeline flow meter and from the combusting means for calculating the energy flow of gas in the pipeline.*

* * * * *